(12) United States Patent
Brasington

(10) Patent No.: US 10,357,619 B1
(45) Date of Patent: Jul. 23, 2019

(54) AUTO-INJECTION DEVICE

(71) Applicant: Chalbourne Brasington, Greenville, SC (US)

(72) Inventor: Chalbourne Brasington, Greenville, SC (US)

(73) Assignee: Chalbourne Brasington, Greenville, SC (US)

( * ) Notice: Subject to any disclaimer, the term of this patent is extended or adjusted under 35 U.S.C. 154(b) by 0 days.

(21) Appl. No.: 15/891,464

(22) Filed: Feb. 8, 2018

(51) Int. Cl.
*A61M 5/32* (2006.01)
*A61M 5/20* (2006.01)

(52) U.S. Cl.
CPC .......... *A61M 5/326* (2013.01); *A61M 5/2033* (2013.01); *A61M 5/3245* (2013.01); *A61M 2005/2013* (2013.01)

(58) Field of Classification Search
CPC .. A61M 5/326; A61M 5/3271; A61M 5/2033; A61M 5/3245; A61M 2005/2013; A61M 2005/3271; A61M 2005/3268; A61M 2005/3267; A61M 25/00; A61M 37/0092; A61M 25/0009; A61M 25/0662; A61M 29/02; A61M 29/00; A61B 17/3478; A61B 17/2202; A61B 17/22
See application file for complete search history.

(56) References Cited

U.S. PATENT DOCUMENTS

| 2,866,458 | A | 12/1958 | Hein, Jr. | |
|---|---|---|---|---|
| 4,031,893 | A | 6/1977 | Kaplan et al. | |
| 4,226,235 | A | 10/1980 | Sarnoff et al. | |
| 4,329,988 | A | 5/1982 | Sarnoff et al. | |
| 4,394,863 | A | 7/1983 | Bartner | |
| 4,723,937 | A | 2/1988 | Sarnoff et al. | |
| 5,092,843 | A | 3/1992 | Monroe et al. | |
| 5,282,793 | A | 2/1994 | Larson | |
| 5,295,965 | A | 3/1994 | Wilmot | |
| 5,307,953 | A | 5/1994 | Regan | |
| 5,549,561 | A | 8/1996 | Hjertman | |
| 5,713,866 | A | 2/1998 | Wilmot | |
| 6,210,369 | B1 | 4/2001 | Wilmot et al. | |
| 6,689,092 | B2 | 2/2004 | Zierenberg et al. | |
| 6,767,336 | B1 * | 7/2004 | Kaplan ................. | A61M 5/326 604/131 |
| 6,805,686 | B1 | 10/2004 | Fathallah et al. | |

(Continued)

FOREIGN PATENT DOCUMENTS

WO    WO 2013050475 A2 *  4/2013  ............ A61M 5/326

*Primary Examiner* — Bhisma Mehta
*Assistant Examiner* — Hamza A Darb
(74) *Attorney, Agent, or Firm* — Dority & Manning, P.A.

(57) ABSTRACT

An auto-injection device including a housing, cartridge, needle, and needle cover. The housing includes longitudinally extending flexible arms. The cartridge moves relative to the housing and contains fluid medicament. The needle is at a proximal end of the device. The needle cover has openings along the longitudinal direction and moves between a first position, a second position, and a third position, wherein the needle is unexposed in the first and third positions and in the second position the needle is exposed. The needle cover is biased towards the third position. An abutment on the at least one longitudinally extending arm of the housing is receivable within the at least one opening along the longitudinal direction of the needle cover when the needle cover is biased into the third position.

18 Claims, 9 Drawing Sheets

(56) References Cited

U.S. PATENT DOCUMENTS

| | | | |
|---|---|---|---|
| 7,314,464 B2* | 1/2008 | Giambattista | A61M 5/002 604/110 |
| 7,442,185 B2 | 10/2008 | Amark et al. | |
| 7,449,012 B2 | 11/2008 | Young et al. | |
| 7,794,432 B2 | 9/2010 | Young et al. | |
| 8,048,035 B2 | 11/2011 | Mesa et al. | |
| 8,449,498 B2 | 5/2013 | Marshall et al. | |
| 8,591,465 B2 | 11/2013 | Hommann | |
| 8,870,827 B2 | 10/2014 | Young et al. | |
| 9,227,016 B2 | 1/2016 | Ekman et al. | |
| 9,427,528 B2 | 8/2016 | Hommann et al. | |
| 9,446,196 B2 | 9/2016 | Hourmand et al. | |
| 9,586,010 B2 | 3/2017 | Mesa et al. | |
| 9,592,350 B2 | 3/2017 | Roberts et al. | |
| 9,636,467 B2 | 5/2017 | Ekman et al. | |
| 9,649,451 B2 | 5/2017 | Beek et al. | |
| 9,694,141 B2 | 7/2017 | Slemmen et al. | |
| 9,724,472 B2 | 8/2017 | Hourmand et al. | |
| 9,737,663 B2 | 8/2017 | Jennings et al. | |
| 9,744,302 B2 | 8/2017 | Travanty | |
| 9,757,523 B2 | 9/2017 | MacDonald et al. | |
| 2004/0039337 A1 | 2/2004 | Letzing | |
| 2005/0020979 A1 | 1/2005 | Westbye et al. | |
| 2013/0296798 A1 | 11/2013 | Roberts et al. | |
| 2014/0081239 A1 | 3/2014 | Cronenberg | |
| 2014/0207106 A1 | 7/2014 | Bechmann et al. | |
| 2014/0257201 A1* | 9/2014 | Geiger | A61M 5/3245 604/263 |
| 2015/0231333 A1 | 8/2015 | Lannan et al. | |
| 2015/0273161 A1 | 10/2015 | Bengtsson et al. | |
| 2017/0143911 A1* | 5/2017 | Roberts | A61M 5/3234 |

\* cited by examiner bad# AUTO-INJECTION DEVICE

FIELD OF THE INVENTION

The present disclosure relates generally to auto-injection devices, and more particularly to an auto-injection device and method for delivering a fluid medicament.

BACKGROUND OF THE INVENTION

Auto-injection devices are utilized in a variety of settings, typically to treat medical emergencies. For example, anaphylaxis is a serious medical emergency that can be fatal if not treated quickly. The most common causes of anaphylaxis include food allergies (e.g., nut or shellfish allergies) and insect bites or stings. Certain medications can also cause anaphylaxis. Symptoms of anaphylaxis include an itchy rash, throat swelling, and low blood pressure. Rapid diagnosis and immediate injection of intramuscular epinephrine is often critical to prevent a fatal outcome, as muscles have larger and more blood vessels than subcutaneous tissue and intramuscular injections usually have faster rates of absorption than subcutaneous or intradermal injections. Death from anaphylaxis occurs most often in teenagers and young adults and is directly related to receiving injected epinephrine too late, inaccurately (e.g., outside the muscle), or not at all. Anaphylaxis most often occurs unexpectedly and in the absence of a trained health care professional. Because exposure is unpredictable, the reaction may occur rapidly, and the patient may not be near medical help at the time of exposure, patients who are subject to severe anaphylaxis must carry epinephrine at all times. It is also necessary that the patient be able to self-administer the epinephrine during an anaphylactic attack in an efficient, simple manner.

Currently available auto-injection devices are generally cylindrical in shape and include a spring-activated concealed needle that, when triggered, springs forward to pierce the skin and deliver a dose of epinephrine or other medicament. Such devices are designed for single dose intramuscular injection for emergency treatment of anaphylaxis and opioid overdose, or for regular treatment of conditions such as multiple sclerosis, diabetes, rheumatoid arthritis, and plaque psoriasis.

There are a number of problems with the aforementioned automatic injection devices. These devices are complex, difficult to use, and expensive. Many patients are noncompliant when prescribed these devices and do not carry one with them at all times for various reasons including problems with size, shape appearance, and cost. These problems can contribute to incorrect use, misuse, and not carrying the unit as prescribed (non-compliance), resulting in adverse outcomes. Therefore, it can be appreciated that currently available automatic injection devices have a number of problems associated with their design and function that could make emergency treatment for avoidable causes of death difficult.

As such, a need currently exists for an improved auto-injection device for rapid injection of a fluid medicament to the desired location.

SUMMARY OF THE INVENTION

Aspects and advantages of the invention will be set forth in part in the following description, or may be obvious from the description, or may be learned through practice of the invention.

In accordance with one embodiment of the present disclosure, an auto-injection device defining a longitudinal direction is contemplated. The auto-injection device includes a housing, a cartridge, a needle, and a needle cover. The housing has at least one longitudinally extending arm flexible between a first position and a second position. The cartridge moves along the longitudinal direction relative to the housing and holds a fluid medicament contained between a stopper and a proximal end of the cartridge. The needle is located at a proximal end of the auto-injection device. The needle cover moves along the longitudinal direction relative to the housing between the proximal end of the auto-injection device and a distal end of the auto-injection device and has at least one opening along the longitudinal direction. The needle cover moves along the longitudinal direction relative to the housing from a first position to a second position, and from the second position to a third position, wherein in the first position the needle is unexposed along the longitudinal direction, in the second position the needle is exposable along the longitudinal direction, and in the third position the needle is again unexposed. The needle cover is biased towards the third position. An abutment on the at least one longitudinally extending arm of the housing can be received within the at least one opening along the longitudinal direction of the needle cover when the needle cover is biased to the third position.

In another embodiment of the present disclosure, the auto-injection device may further include an opening that is located along the proximal end of the needle cover, wherein the proximal end of the needle is movable through the opening when the needle cover is moved to the second position.

In one particular embodiment of the present disclosure, a needle sheath is disposed between the proximal end of the needle cover and the proximal end of the cartridge, the needle being at least partially disposed within the needle sheath. The needle sheath is pierced by the needle when the needle cover is moved from the first position to the second position.

In yet another embodiment of the present disclosure, the at least one longitudinally extending arm of the housing can be flexible between a first position and a second position, such that in the first position the at least one longitudinally extending arm can extend inwardly from the housing at a first angle and in the second position the at least one longitudinally extending arm can extend inwardly from the housing at a second angle. For instance, the first angle can be from about 0 degrees to about 5 degrees, and the second angle can be from about 5 degrees to about 15 degrees.

In still another embodiment of the present disclosure, the needle can be fixed to the cartridge.

In an additional embodiment of the present disclosure, the auto injection device can further include at least one outwardly extending abutment on an exterior surface of the cartridge and at least one projection extending along an interior surface of the needle cover. The at least one outwardly extending abutment can be configured to engage the at least one projection extending along an interior surface of the needle cover.

In an additional embodiment of the present disclosure, the auto injection device can further include a removable safety. When in place on the auto-injection device, the removable safety can prevent movement of the needle cover from the first position to the second position, can prevent movement of the cartridge from the first position to the second position, or both.

In still another embodiment of the present disclosure, the auto injection device can further include a plunger, a proximal end of the plunger being attached to the stopper, an end stop, and a retainer. The safety can be configured to be removably inserted into a distal end of the plunger, such that when the safety is removed from the plunger, the retainer is movable towards the distal end of the auto-injection device such that the end stop is engageable around the distal end of the plunger and the plunger is then removable from within the retainer. The retainer can be movable towards the distal end of the auto-injection device by the distal end of the needle cover, such that the distal end of the needle cover abuts against the retainer when the needle cover moves to the second position.

In yet another embodiment of the present disclosure, the auto injection device can further include a first biasing element and a second biasing element. A proximal end of the first biasing element can exert a force on a circumferential flange of the plunger and a distal end of the first biasing element can exert a force on the retainer. A proximal end of the second biasing element can exert a force on a circumferential flange on an exterior surface of the needle cover and a distal end of the second biasing element can exert a force on a flange on an interior surface of the housing.

In accordance with another embodiment of the present disclosure, a method for delivering a dose of fluid medicament via an auto-injection device is contemplated. The auto-injection device defines a longitudinal direction and includes a housing having at least one longitudinally extending arm, the at least one longitudinally extending arm being flexible between a first position and a second position; a cartridge movable along the longitudinal direction relative to the housing, the cartridge containing a fluid medicament contained between a stopper and a proximal end of the cartridge, wherein the stopper includes a recess located at a distal end of the stopper; a needle located at a proximal end of the auto-injection device; a needle cover movable along the longitudinal direction relative to the housing between the proximal end of the auto-injection device and a distal end of the auto-injection device, the needle cover comprising at least one opening along the longitudinal direction; and a plunger, a proximal end of the plunger being engaged in the recess at the distal end of the stopper. The method first includes pressing the proximal end of the auto-injection device against a surface of skin, wherein the longitudinal direction of the auto-injection device is generally perpendicular to the surface of skin and the at least one longitudinally extending arm is in the first position, such that the needle cover moves from a first position to a second position and the cartridge moves from a first position to a second position. Next, the method includes piercing the surface of skin and underlying tissue with a proximal end of the needle by continuing to press the proximal end of the auto-injection device against the surface of the skin such that the cartridge moves from a second position to a third position, and delivering the fluid medicament by pressing the proximal end of the auto-injection device against the surface of skin until a circumferential flange of the plunger abuts a circumferential flange on the interior surface of the cartridge.

In one particular embodiment of the present disclosure, the at least one longitudinally extending arm can extend inwardly from the housing at an angle of from about 0 degrees to about 5 degrees in the first position and from about 5 degrees to about 15 degrees in the second position.

In another particular embodiment of the present disclosure, the proximal end of the cartridge includes an opening, wherein a distal end of the needle is contained within the opening. A needle sheath is disposed between the proximal end of the needle cover and the proximal end of the cartridge, the needle being at least partially disposed within the needle sheath, wherein the needle sheath material is pierced by the needle by pressing the proximal end of the auto-injection device against the surface of skin until the needle cover moves from the first position to the second position.

In still another embodiment of the present disclosure, the auto-injection device can further include an end stop, a retainer, and a safety. The safety can be removably inserted into a distal end of the plunger such that when in place on the auto-injection device, the safety can prevent the needle cover from sliding against the housing, can prevent the cartridge from sliding against the needle cover, or both. The method can further include removing the safety prior to positioning the proximal end of the auto-injection device against the surface of skin such that when the needle cover moves from a first position to a second position, the distal end of the needle cover moves the retainer towards the distal end of the auto-injection device, the end stop engages around the distal end of the plunger, and the plunger is then removable from the retainer.

In yet another embodiment of the present disclosure, a proximal end of a first biasing element can exert a force on a circumferential flange of the plunger and a distal end of the first biasing element can exert a force on the retainer to facilitate delivery of the fluid medicament when the cartridge is in the third position. A proximal end of a second biasing element can exert a force on a circumferential flange on an exterior surface of the needle cover and a distal end of the second biasing element can exert a force on a circumferential flange on an interior surface of the housing to bias the needle cover towards the third position.

In an additional embodiment of the present disclosure, the method can further include removing the proximal end of the auto-injection device from the surface of skin after the fluid medicament is delivered such that the needle cover can be biased to a third position and the at least one longitudinally extending arm of the housing is received within the at least one opening along the longitudinal direction of the needle cover, such that the needle is unexposed along the longitudinal direction and at least one longitudinally extending arm of the housing can be moved into the second position.

In one more embodiment of the present disclosure, the fluid medicament can contain epinephrine or naloxone.

These and other features, aspects and advantages of the present disclosure will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present disclosure, including the best mode thereof to one skilled in the art, is set forth more particularly in the remainder of the specification, including reference to the accompanying figures, in which.

Figure 1:
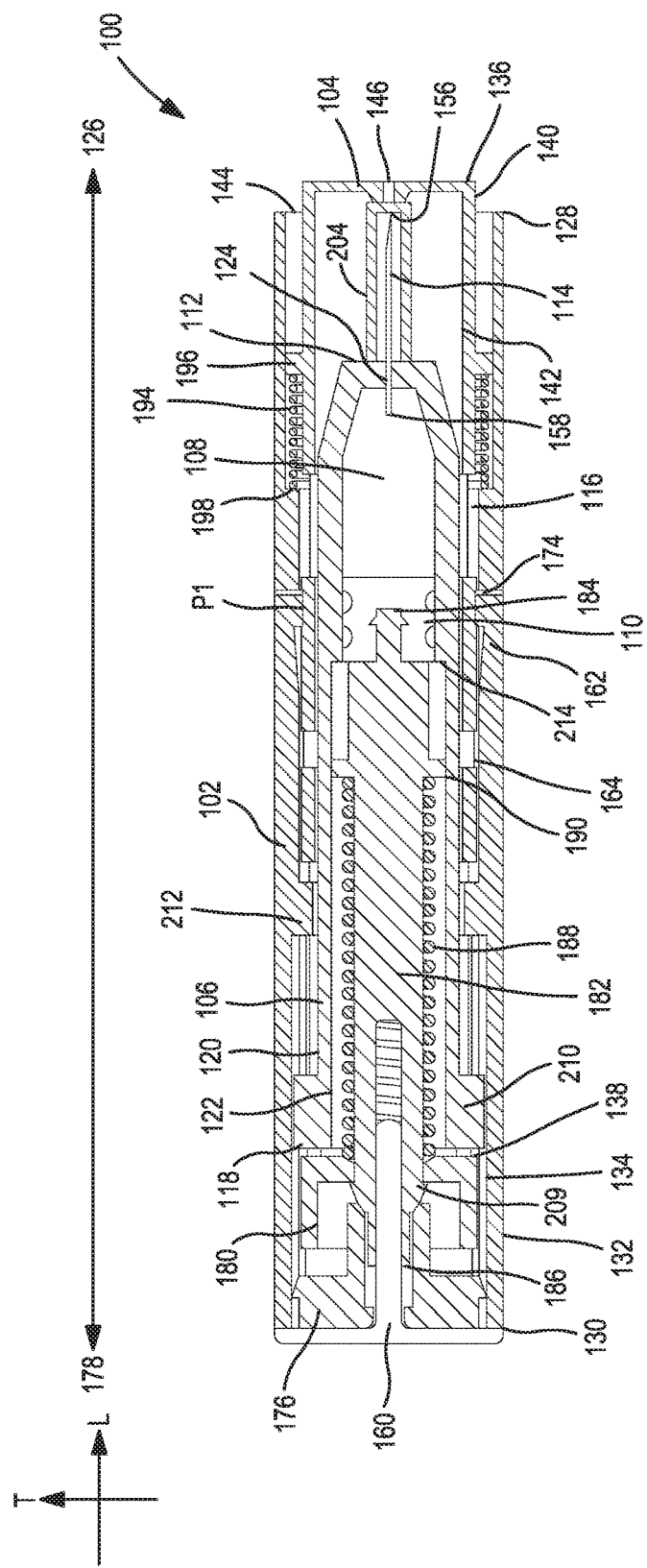
FIG. 1 depicts a longitudinal cross-sectional view of an exemplary auto-injection device having a housing at least one longitudinally extending arm, a cartridge holding a fluid medicament contained between a stopper and a proximal end of the cartridge, a needle, a needle cover.

Repeat use of reference characters in the present specification and drawings is intended to represent the same or analogous features or elements of the present disclosure.

DETAILED DESCRIPTION OF REPRESENTATIVE EMBODIMENTS

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present disclosure without departing from the scope or spirit of the invention. For instance, features illustrated or described as part of one embodiment can be used with another embodiment to yield a still further embodiment. Thus, it is intended that the present disclosure covers such modifications and variations as come within the scope of the appended claims and their equivalents.

Generally speaking, the present disclosure is directed to an auto-injection device for the delivery of a fluid medicament and a method for delivering fluid medicament (e.g., intramuscularly, subcutaneously, etc.) using an auto-injection device. The auto-injection device can deliver the fluid medicament by piercing a surface of skin and delivering the fluid medicament.

The fluid medicament contained within the auto-injection device can be any fluid medicament that can be delivered intramuscularly or subcutaneously. In one particular embodiment, such as when the auto-injection device is used to treat anaphylaxis, the fluid medicament can be epinephrine. Epinephrine, also known as 4-[(1R)-1-Hydroxy-2-(methylamino)ethyl]-1,2-benzenediol, is the active principle of the adrenal medulla and an endogenous catecholamine which acts directly on both alpha and beta adrenergic receptors. When used in pharmaceutical compositions, epinephrine can act as a non-selective alpha and beta adrenergic agonist and can work rapidly to improve breathing, stimulate the heart, raise dropping blood pressure, reverse hives, and reduce swelling of the face, lips, and throat. Uses for epinephrine include emergency treatment of allergic reactions (Type 1), including anaphylaxis, induction and maintenance of mydriasis during intraocular surgery, treatment of bronchospasm, sensitivity reactions, cardiac arrhythmias, GI and renal hemorrhage, superficial bleeding, premature labor, hypoglycemia, and cardiogenic, hemorrhagic, and traumatic shock. Epinephrine can also be used to increase blood flow in ACLS during CPR, as an adjunct to local anesthesia, and for radiographic uses. Although the use of the auto-injection device of the present disclosure to deliver epinephrine is described herein, it is to be understood that the auto-injection device and its method of use can be utilized in conjunction with any fluid medicament that can be delivered intramuscularly or subcutaneously. For example, naloxone is another fluid medicament that can be delivered using an auto-injection device as described herein, for emergency treatment of an opioid overdose. When used in pharmaceutical compositions, naloxone binds to opioid receptors and can reverse and block the effects of other opioids on the central nervous system and respiratory system to improve breathing, stimulate the heart, raise blood pressure, and alleviate itchiness.

Referring to FIGS. 1-5, an auto-injection device according to embodiments of the present disclosure is shown prior to use. Generally, FIG. 1 depicts a cross-sectional view of an exemplary auto-injection device 100 prior to use taken along a plane extending through line A-A' shown in FIG. 2, where the auto-injection device 100 includes a housing 102, a needle cover 104, a cartridge 106 containing a fluid medicament 108 contained between a stopper 110 and a proximal end 112 of the cartridge 106, and a needle 114. The auto-injection device 100 defines a longitudinal direction L in which the housing 102, needle cover 104, cartridge 106, and needle 114 extend, as well as a transverse direction T. The auto-injection device 100 can include a viewing window 116 through which the cartridge 106 can be observed, where the fluid medicament 108 may be visible through the viewing window 116 prior to use. Further, the cartridge 106 includes a distal end 118, an exterior surface 120, and an interior surface 122. Additionally, the cartridge includes an opening 124 in its proximal end 112 that allows for installation of the needle 114.

As shown in FIGS. 1-5, the needle cover 104 is located towards a proximal end 126 of the auto-injection device 100. The housing 102 includes a proximal end 128, a distal end 130, an exterior surface 132, and an interior surface 134. The needle cover 104 includes a proximal end 136, a distal end 138, an exterior surface 140, and an interior surface 142. The proximal end 128 of the housing 102 includes an opening 144, wherein the needle cover 104 extends therethrough. The proximal end 136 of the needle cover 104 also includes an opening 146. The needle 114 is held within the opening 124 in the proximal end 112 of the cartridge 106, within an interior space formed between the proximal end 136 of the needle cover 104 and the proximal end 112 of the cartridge 106 and is thus unexposed along the longitudinal direction L. As discussed in more detail below, the needle cover 104 is movable along the longitudinal direction L with respect to the housing 102 between a first position L1 and a second position L2, and between the second position L2 and a third position L3. The needle cover 104 is moved from the proximal end 126 of the auto-injection device 100 towards the distal end 178 of the auto-injection device when the needle cover 104 is moved from the first position L1 to the second position L2, and is moved from the distal end 178 of the auto-injection device towards the proximal end 126 of the auto-injection device 100 when the needle cover 104 is moved from the second position L2 to the third position L3. Thus, in the second position L2, the proximal end 136 of the needle cover 104 is closer to the proximal end 128 of the housing than in the first position L1, while in the third position L3, the proximal end 136 of the needle cover 104 is farther from the proximal end 128 of the housing than in the first position L1. The cartridge 106 is movable with respect to the housing 102 along the longitudinal direction L between a first position C1 and a second position C2 and between the second position C2 and a third position C3 The cartridge 106 is also moved from the proximal end 126 of the auto-injection device 100 towards the distal end 178 of the auto-injection device when the cartridge is moved from the first position C1 to the second position C2, and is moved from the distal end 178 of the auto-injection device towards the proximal end 126 of the auto-injection device 100 when the cartridge is moved from the second position C2 to the third position C3. Thus, in the first position C1, the proximal end 112 of the cartridge 106 is closer to the proximal end 128 of the housing than in the second position C2, and in the third position C3, the proximal end 112 of the cartridge 106 is closer to the proximal end 128 of the housing than in the first position C1. As such, when the needle cover 104 is moved from the first position L1 to the second position L2, the cartridge 106 is also moved from the first position C1 to the second position C2, the cartridge 106 is then movable to the third position C3, as will be further described below, and a proximal end 156 of needle 114 can pass through the opening 146 as the needle 114 is fixed to the proximal end 112 of the cartridge 106 between its proximal end 156 and its distal end 158, such as with an epoxy or other suitable sealant or bonding material. Thus, the needle 114 is "exposable" when the needle cover 104 is moved from the first position L1 to the second position L2, such that the needle 114 can be subsequently exposed, but may or may not be exposed depending on the position of other elements besides the needle cover 104, such as the position of the cartridge 106.

Figure 3:
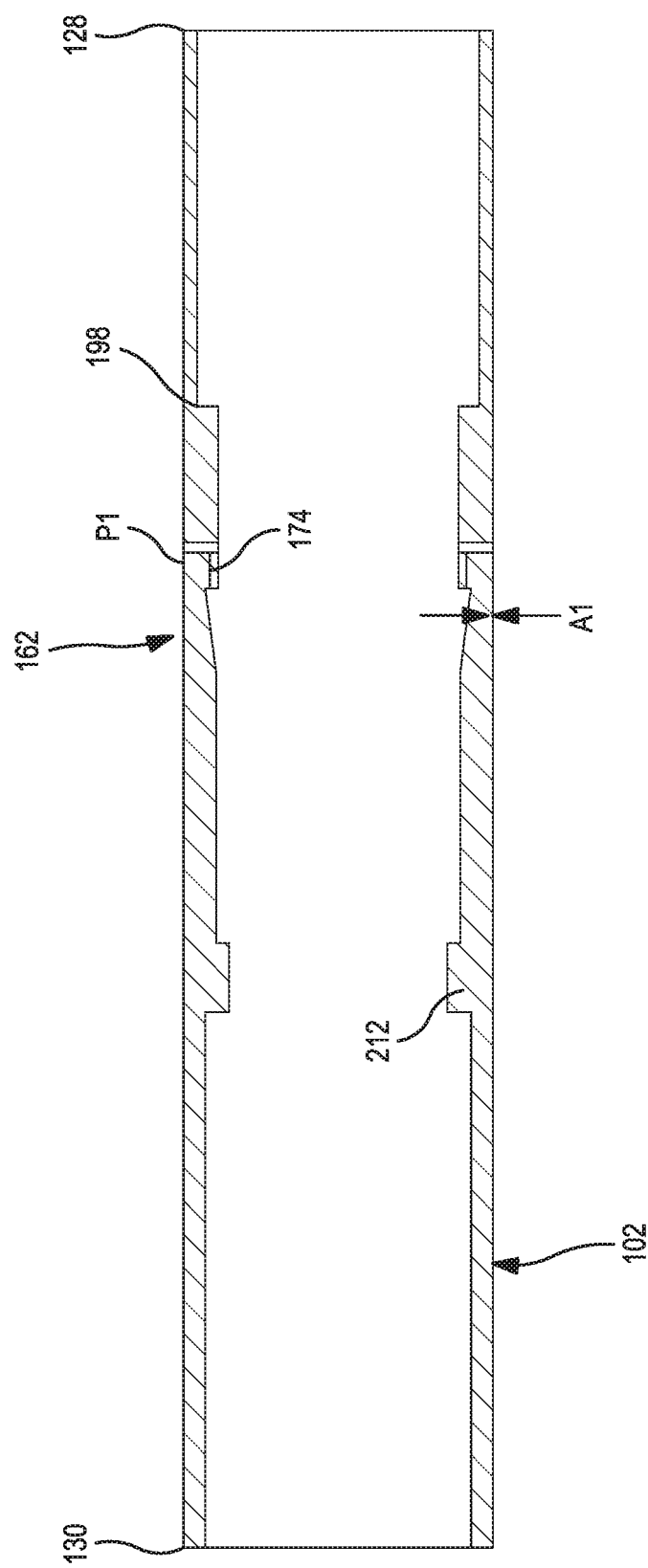
FIG. 3 depicts a cross-sectional view of the housing of the auto-injection device of FIG. 1.

In addition, the auto-injection device 100 can include a removable safety 160 that, when installed, can lock the needle cover 104 such that it is not movable with respect to the housing 102, and can lock the cartridge 106 such that it is not movable with respect to housing 102 such that the needle 114 does not unintentionally pass through the opening 146. The auto-injection device 100 can also include one or more longitudinally extending arms 162 of housing 102, hereinafter referred to as "arms 162," located along the longitudinal direction L, and openings 164 of needle cover 104, located along the longitudinal direction L. The arms 162 are biased such that they extend inwardly and are flexible between a first position P1 and a second position P2, such that in the first position P1 the arms 162 extend inwardly from the exterior surface 132 of the housing 102 at a first angle A1, and in the second position P2 the arms 162 extend inwardly from the exterior surface 132 of the housing 102 at a second angle A2. The first angle A1 may be from about 0 degrees to about 5 degrees and the second angle A2 may be from about 5 degrees to about 15 degrees. It can be appreciated throughout the specification that "about" is intended to mean within 10% of the range end values. As such, it may be appreciated that the arms 162 only slightly extend outwardly from the exterior surface 132 of the housing 102, or not at all, such that a user will not feel the arms 162 underneath a decorative wrapping during use of the auto-injection device 100. FIG. 3 shows the cross-section of the housing 102 through the plane extending through line A-A' and particularly shows the arrangement of the arms 162 of the housing 102 in the first position P1 at first angle A1, wherein the arms 162 are substantially in-line with the housing 102. An abutment 174 on the end of each of the arms 162 may engage the openings 164 of needle cover 104 and prevent reuse of the auto-injection device 100 by preventing the return of the needle cover 104 to the second position L2 after the needle cover 104 has been biased into the third position L3. As such, the arms 162 provide a safety measure to prevent the unintentional reuse of the auto-injection device 100.

Further, the auto-injection device 100 can also include an end stop 176 that is positioned at a distal end 178 of the auto-injection device 100, a retainer 180, and a plunger 182. The plunger 182 includes a proximal end 184 and a distal end 186. The proximal end 184 of the plunger 182 is received within the stopper 110 and the distal end 186 of the plunger 182 is configured to receive the removable safety 160. When the safety 160 is removed from the plunger 182, the retainer 180 is movable towards the distal end 178 of the of the auto-injection device 100 by the distal end 138 of the needle cover 104 when the needle cover 104 moves from the first position L1 to the second position L2, such that the end stop 176 engages around the distal end 186 of the plunger 182. As such, it may be appreciated that the needle cover 104 is movable to be in direct contact with the retainer 180.

Additionally, a first biasing element 188 (e.g., compression spring, a compressed gas, etc.) can be included within the auto-injection device 100 and positioned between the retainer 180 and a circumferential flange 190 on the plunger 182, where the first biasing element 188 can be in a compressed state when the needle cover 104 is in the initial or first position L1 and remains compressed when the needle cover is moved from the first position L1 towards the second position L2. Further, a second biasing element 194 (e.g., a compression spring, a compressed gas, etc.) can be included within the auto-injection device 100 and positioned between a circumferential flange 196 on the exterior surface 140 of the needle cover 104 and a circumferential flange 198 on the interior surface 134 of the housing 102, where the second biasing element 194 can be in a compressed state when the needle cover 104 is in the first position L1 and is further compressed when the needle cover 104 is moved from the first position L1 towards the second position L2.

Figure 4:
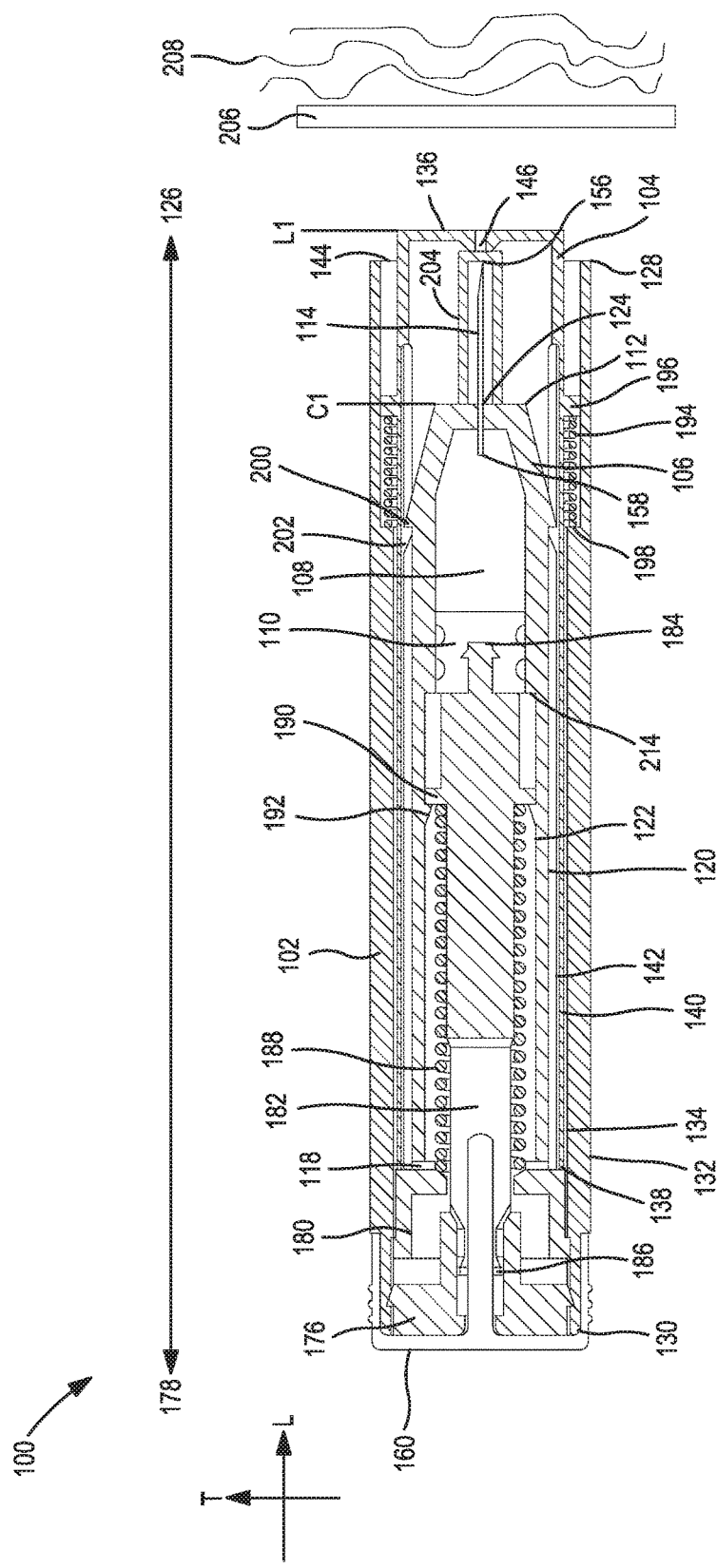
FIG. 4 depicts an alternate cross-sectional view of the auto-injection device of FIG. 1.

In its unused state, the auto-injection device 100 is assembled such that the first position L1 of the needle cover 104 is between the second position L2 and the third position L3, with the needle cover 104 being biased towards the third position L3 by the second biasing element 194. From FIG. 4, showing a cross-sectional view of the device 100 along a plane extending through line B-B', it can be appreciated that movement of the needle cover 104 towards a proximal end 126 of the auto-injection device 100 is limited by outwardly extending abutments 200 on the exterior surface 120 of the cartridge 106 that engage projections 202 extending along the interior surface 142 of the needle cover 104. It can further be appreciated that the cartridge 106 is prevented from moving towards the proximal end 126 of the auto-injection device 100 relative to the plunger 182 by the circumferential flange 190 on the plunger 182 that engages projections 192 on the interior surface 122 of the cartridge 106. From the figures, it may additionally be appreciated that a needle sheath 204 may be disposed around the needle between the proximal end 112 of the cartridge 106 and the proximal end 136 of the needle cover 104 to ensure sterility of the needle 114 and to protect the needle 114 from physical damage prior to use. Such a needle sheath 204 may be made out of a flexible and/or compressible material such that it may be punctured by the needle 114 and compressed when the needle cover 104 moves from the first position L1 to the second position L2 during use.

Additionally, the housing 102, needle cover 104, and cartridge 106 can be formed from any suitable plastic (e.g., polycarbonate, a polyolefin such as a cyclic olefin polymer or a cyclic olefin copolymer, a polyethylene or polypropylene, a polystyrene, etc.). Further, because the cartridge 106 can be formed from a plastic as opposed to glass, the present disclosure contemplates an auto-injection device that does not require the cartridge 106 to be contained within a protective casing (e.g., the auto-injection device 100 is free of a casing or container) such that the cartridge 106 can come into direct contact with the needle cover 104 and/or the housing 102. In other words, the housing 102 and/or the needle cover 104 can instead serve as a protective casing to hold the cartridge 106 as opposed to a separate, distinct casing surrounding the cartridge 106. It can be appreciated that such a cartridge may reduce the manufacturing cost of such an auto injection device to improve patient non-compliance due to costs.

Figure 5:
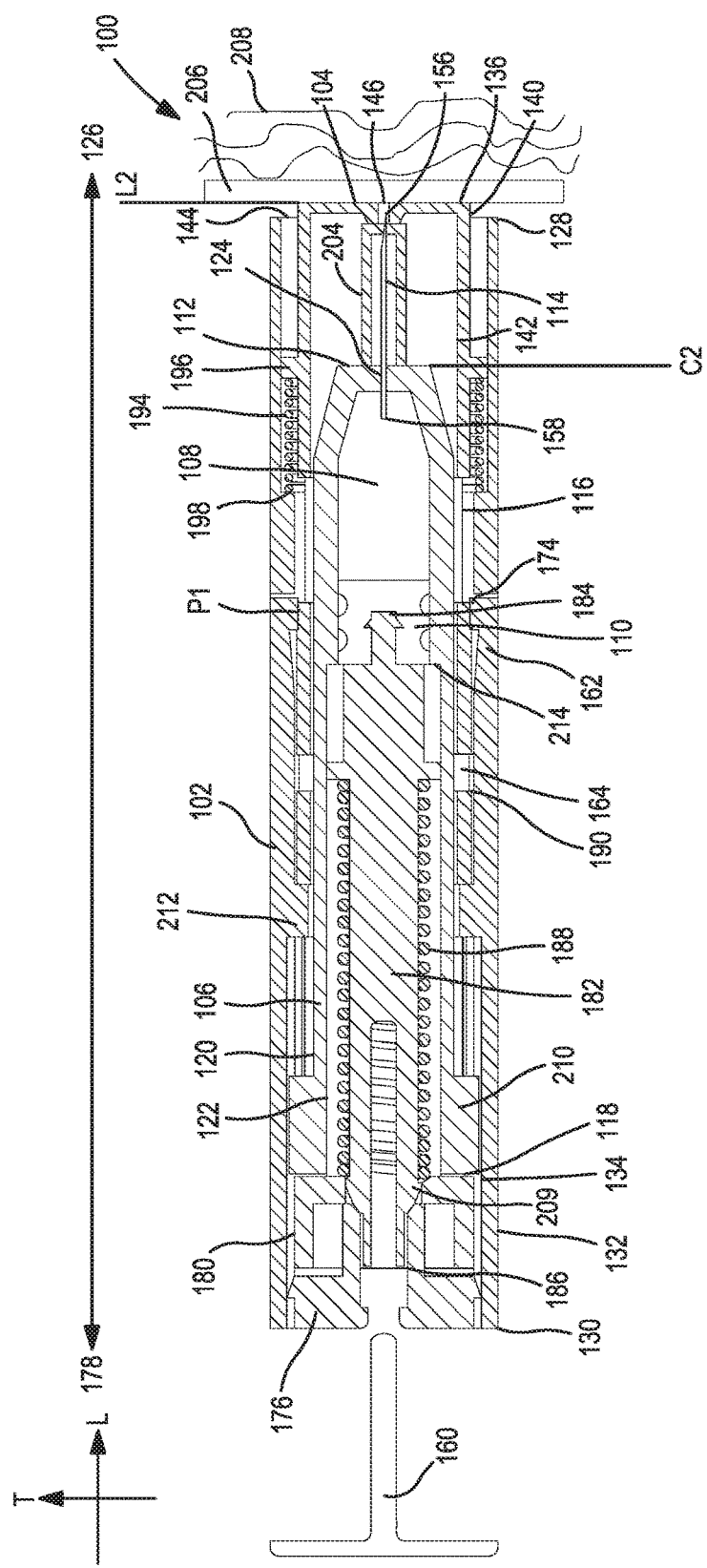
FIG. 5 depicts the auto-injection device of FIG. 1 immediately after a safety is removed and the needle cover is pushed against the injection location and biased towards its second position before the delivery of the fluid medicament.

In FIG. 5, showing the cross-sectional view of the auto injection device 100 along the plane extending through line A-A', the safety 160 has been removed and the proximal end 136 of the needle cover 104 is firmly pressed (i.e., with about 5 pounds of force or less) against the surface of skin 206 while holding the housing 102 of the auto-injection device 100 so that the longitudinal direction L of the auto-injection device 100 is generally perpendicular to the surface of skin 206. The needle cover 104 is moved with the cartridge 106, retainer 180 and plunger 182 along the longitudinal direction L relative to the housing 102 towards the distal end 178 of the auto-injection device 100 as described below. The distal end 138 of the needle cover 104 pushes the retainer 180 as the needle cover 104 is pressed against the surface of skin 206. Flares 209 on the plunger 182 initially rest on the retainer 180 (as shown in FIG. 1), such that the plunger 182 is moved as the retainer 180 is moved towards a distal end 178 of the auto-injection device 100. As the circumferential flange 190 of the plunger 182 abuts against the projections 192 on the interior surface 122 of the cartridge 106, the cartridge 106 also moves with the plunger 182, such that the cartridge 106 is moved into its second position C2 as the needle cover 104 is moved into its second position L2. The retainer 180 is pushed towards the end stop 176 such that the end stop 176 engages around the distal end 186 of the plunger 182 and the retainer 180 is then removable from around the plunger 182. The distal end 186 of the plunger 182 is compressed within the end stop 176 such that the first biasing element 188 is then capable of biasing the plunger 182 such that the plunger 182 is removable from within the retainer 180. The cartridge 106 and the plunger 182 are then able to be biased towards the proximal end 126 of the auto-injection device 100 by the first biasing element 188 expanding in the longitudinal direction L such that the cartridge moves from its second position C2, as discussed with reference to FIG. 6.

Figure 6:
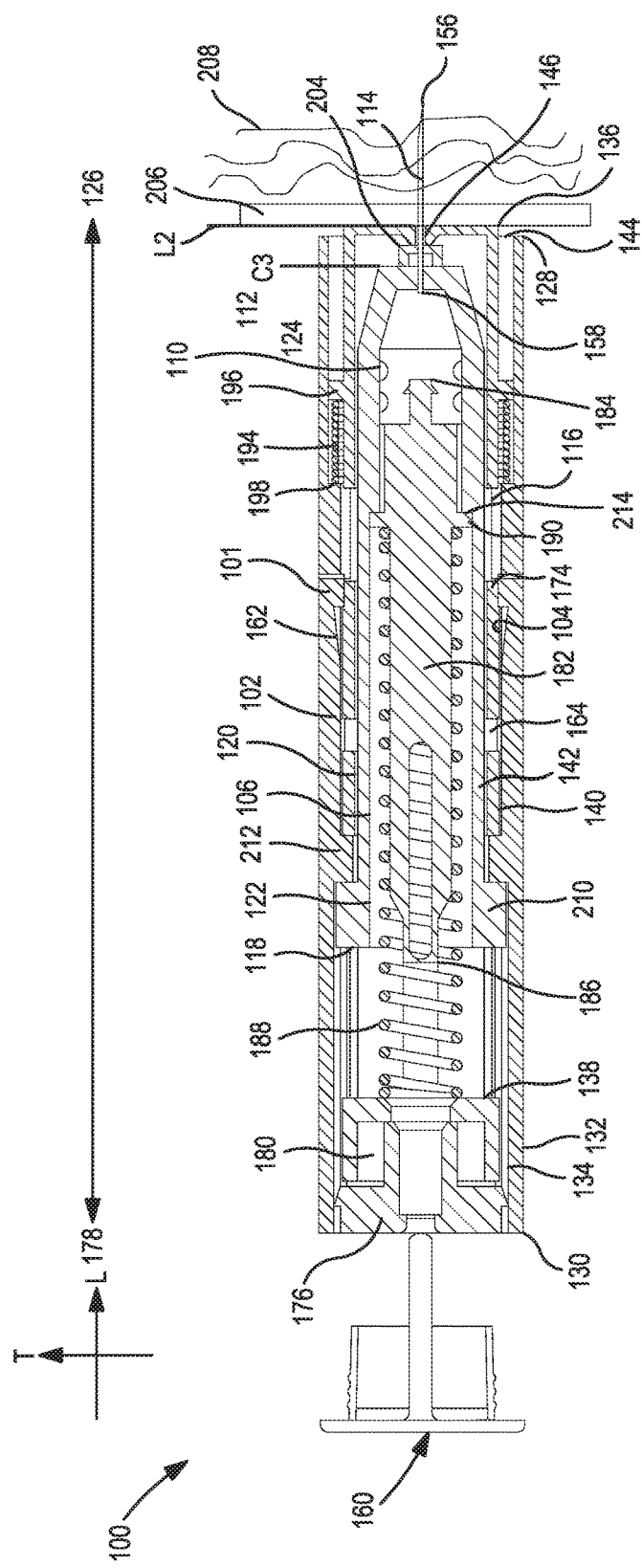
FIG. 6 depicts the auto-injection device of FIG. 1 after a safety is removed and the needle cover is pushed against the injection location and biased towards the second position, and a biasing element has caused movement of the stopper towards the proximal end of the cartridge to deliver the fluid medicament.

Next, FIG. 6 depicts the auto-injection device of FIG. 1 along the plane extending through line A-A' after the safety 160 is removed, the needle sheath 204 is pierced, and the needle cover 104 is moved from its first position L1 into a second position L2 so that the proximal end 156 of the needle 114 is now exposed along the longitudinal direction L, has pierced a surface of skin 206, and contacted muscle 208. To arrive at such an orientation, once the distal end 186 of the plunger 182 is compressed within the end stop 176, the plunger 182 is pulled through and removed from within the retainer 180 such that the cartridge 106 and the plunger 182 are together biased towards the proximal end 126 of the auto-injection device 100 by the first biasing element 188 expanding in the longitudinal direction L. The cartridge moves towards the proximal end 126 of the auto-injection device 100 from its second position C2 until projections 210 formed on the exterior surface 120 of the cartridge 106 abut ledges 212 formed on the interior surface 134 of the housing 102, whereby the cartridge 106 is in its third position C3 and the proximal end 156 of the needle 114 has passed through the opening 146 in the proximal end 136 of the needle cover 102 and has pierced through the needle sheath 204 and the surface of skin 206 and has entered the muscle 208. The first biasing element 188 continues to expand and bias the plunger 182 when the cartridge 106 is in its third position C3, whereby the fluid medicament 108 can now pass from the cartridge 106, through the distal end 158 of the needle 114, and out of the proximal end 156 of the needle 114 into the muscle 208, until the circumferential flange 190 on the plunger 182 abuts a circumferential flange 214 on the interior surface 122 of the cartridge 106, whereby all the fluid medicament 108 has been delivered.

It can be additionally appreciated, as shown in FIG. 6, that the needle sheath 204 is fully compressed between the proximal end 112 of the cartridge 106 and the proximal end 136 of the needle cover 104 when the cartridge 106 is in its third position C3 and the needle cover 104 is in the second position L2.

Figure 2:
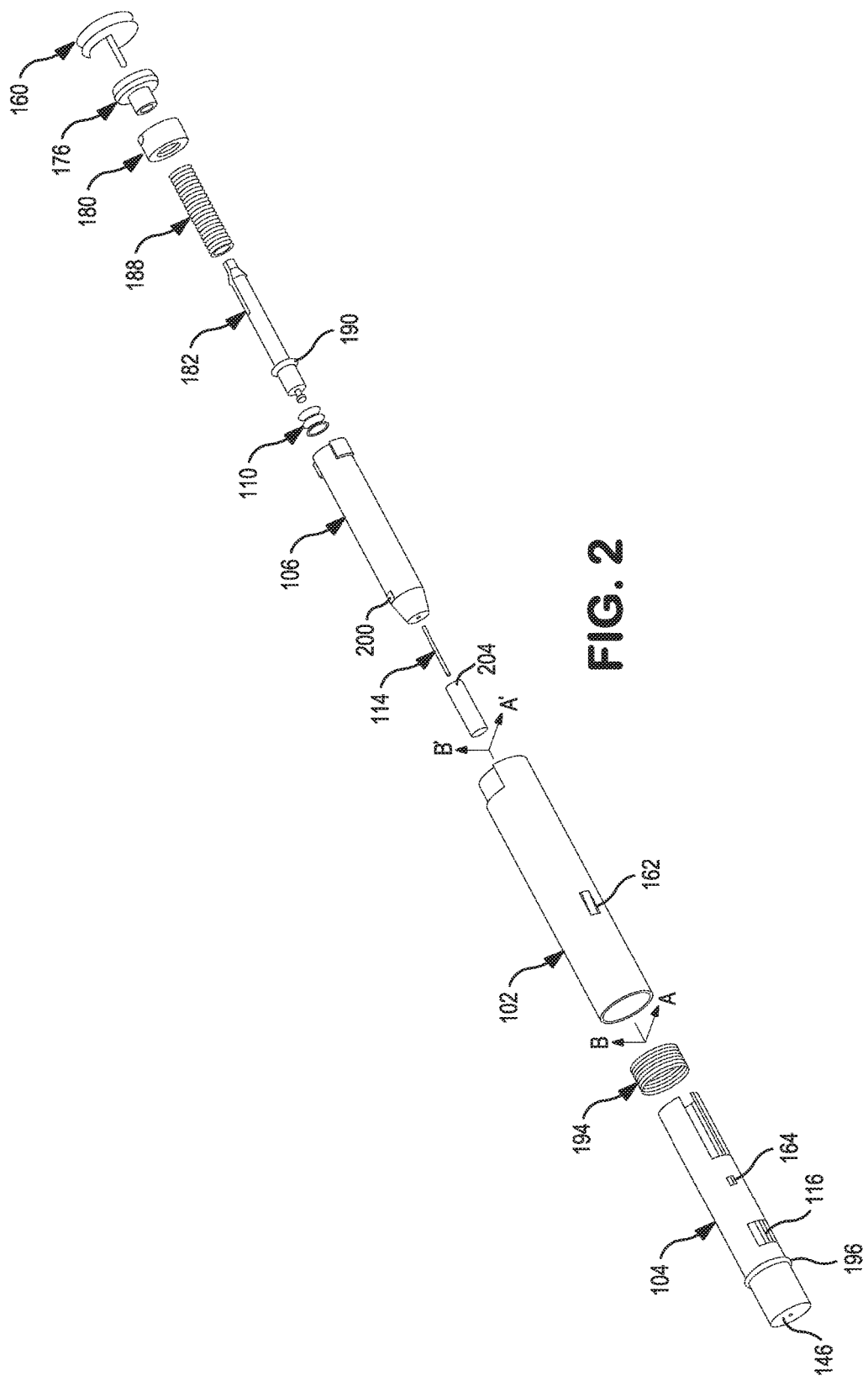
FIG. 2 depicts an exploded view of the exemplary auto-injection device of FIG. 1.
Figure 7:
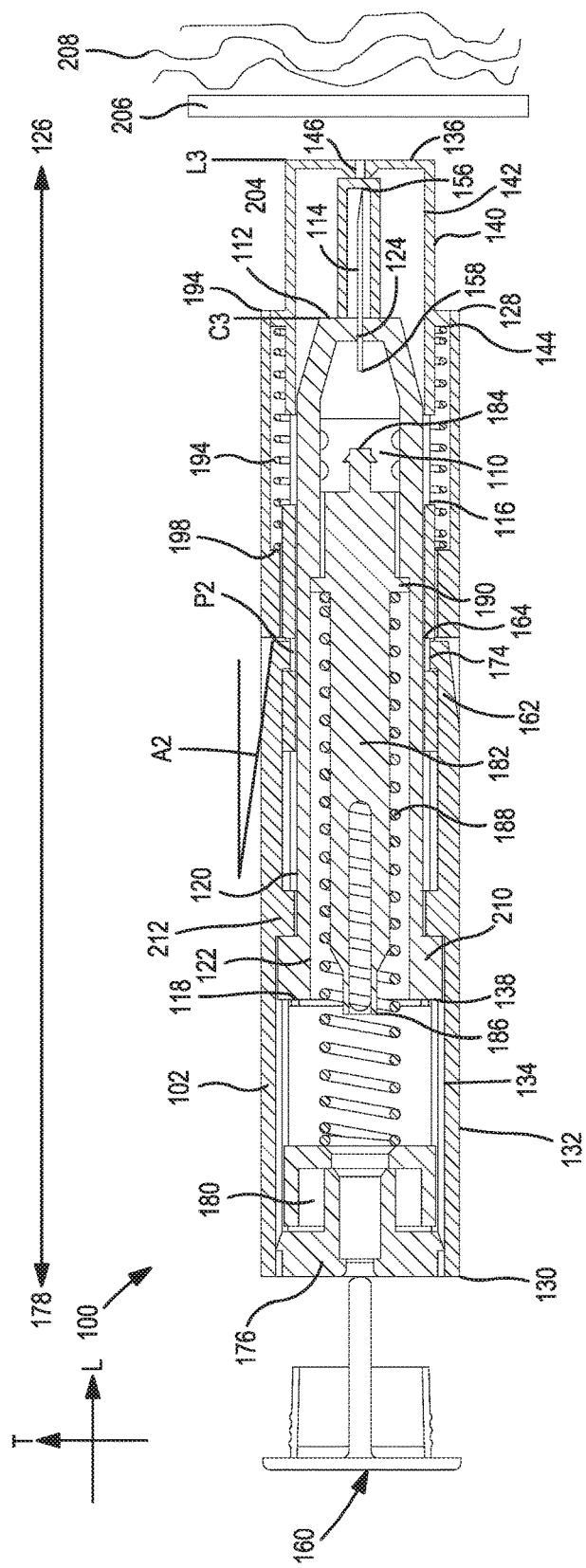
FIG. 7 depicts the auto-injection device of FIG. 1 after the needle cover is removed from the injection location, the needle cover is biased into the third position, and the housing is locked into the needle cover.
Figure 8:
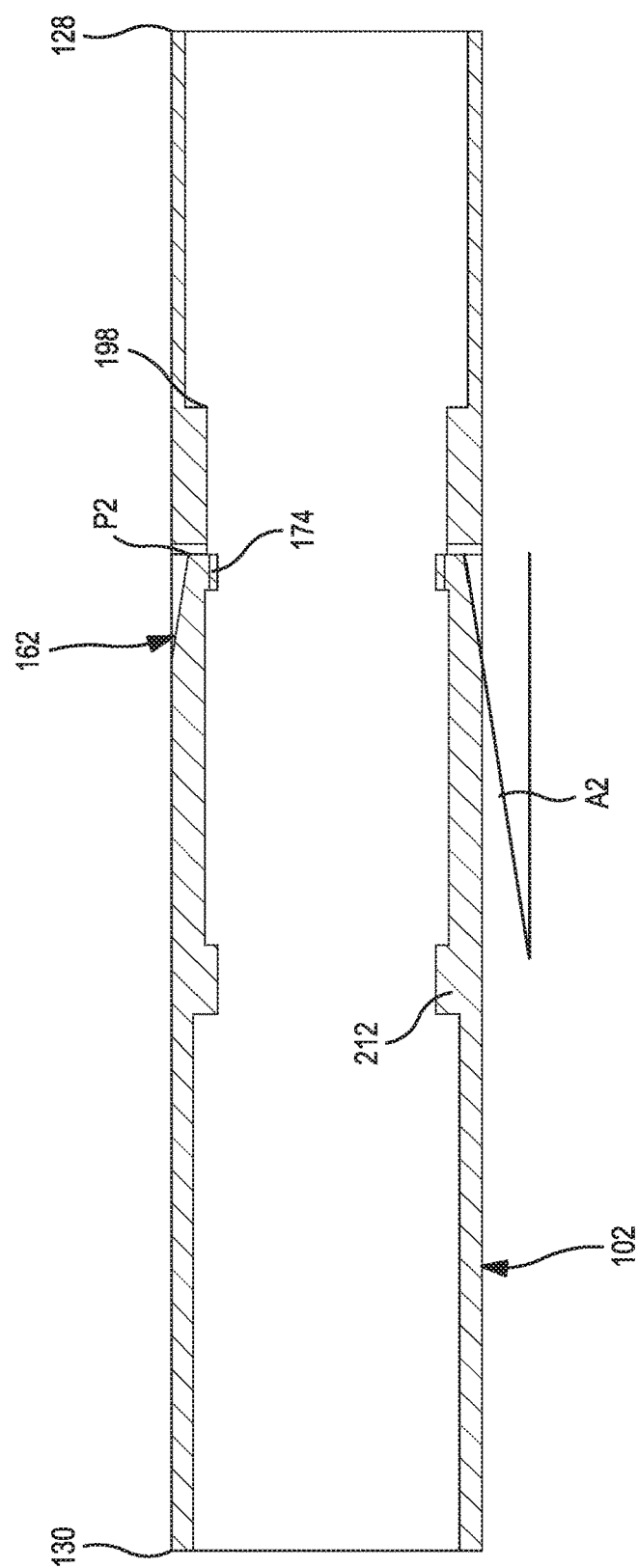
FIG. 8 depicts a cross-sectional view of the housing of the auto-injection device of FIG. 7.
Figure 9:
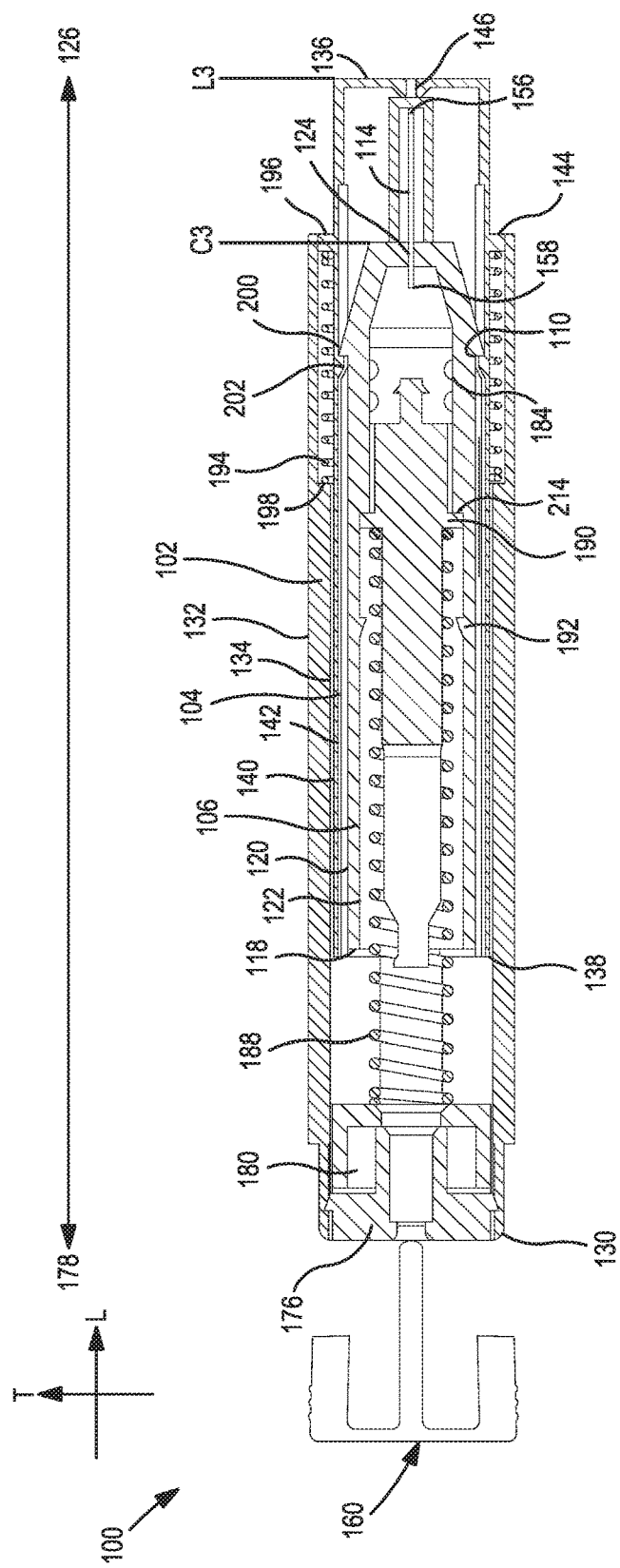
FIG. 9 depicts an alternate view of the auto-injection device of FIG. 7.

Turning now to FIGS. 7-9, FIG. 7 shows a cross sectional view of the auto-injection device of FIG. 1 along the plane extending through line A-A' shown in FIG. 2 after the fluid medicament 108 has been delivered, the proximal end 136 of the needle cover 104 has been removed from the surface of skin 206, the needle cover 104 has been biased into its third position L3, and abutments 174 on the arms 162 of the housing 102 have engaged in the openings 164 of the needle cover 104 so that the proximal end 156 of the needle 114 is not exposed along the longitudinal direction L and that the needle cover 104 is prevented from moving. For the needle cover 104 to arrive at its third position L3, the user lifts the auto-injection device 100 away from the surface of skin 206 such that the second biasing element 194 expands in the longitudinal direction L and biases the needle cover 104 into its third position L3. While moving towards the third position L3, the openings 164 in the needle cover 104 are moved past the abutments 174 on the arms 162 of the housing 102, such that when the needle cover 104 arrives in the third position L3, the abutments 174 move from the first position P1, where the arms 162 extend inwardly from the exterior surface 132 of the housing 102 at the first angle A1, to the second position P2, where the arms 162 extend inwardly from the exterior surface 132 of the housing 102 at the second angle A2, such that the abutments 174 engage the openings 164. This position of the arms 162 is particularly shown in FIG. 8, showing the cross-sectional view of the housing 102 along the plane extending through line A-A', wherein the arms 162 are in a second position P2 at an angle A2 such that the arms are no longer in-line with the housing 102.

It can again be appreciated from FIG. 9, showing the cross-sectional view of the device 100 along the plane extending through line B-B' shown in FIG. 2, that the outwardly extending abutments 200 on the exterior surface 120 of the cartridge 106 engage projections 202 extending along the interior surface 142 of the needle cover 104 to prevent movement of the needle cover 104 towards the proximal end 126 of the auto-injection device 100 and relative to the cartridge 106.

As described above, the present disclosure contemplates an auto-injection device having a housing with arms that engage a needle cover after use to prevent accidental reuse and wherein the needle cover directly contacts a retainer. Such an auto-injection device improves the safety of the auto-injection device after use and significantly reduces the number of parts required for such a device which reduces the corresponding costs of manufacture and ultimately the cost for the user. In other words, by locking the needle cover in place with arms of the housing after use and by having a needle cover in direct contact with a retainer, the auto-injection device of the present disclosure enables delivery of the fluid medicament in a safe and cost-effective manner.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An auto-injection device defining a longitudinal direction, the auto-injection device comprising:
    a housing comprising at least one longitudinally extending arm, the at least one longitudinally extending arm being flexible between a first position and a second position;
    a cartridge movable along the longitudinal direction relative to the housing, the cartridge comprising a fluid medicament contained between a stopper and a proximal end of the cartridge;
    a needle located at a proximal end of the auto-injection device; and
    a needle cover movable along the longitudinal direction relative to the housing between the proximal end of the auto-injection device and a distal end of the auto-injection device, the needle cover comprising at least one opening along the longitudinal direction,
    wherein the needle cover is movable along the longitudinal direction relative to the housing from a first covering position to a second uncovering position and from the second uncovering position to a third covering position, the needle cover being biased towards the third covering position, wherein the needle is unexposed along the longitudinal direction when the needle cover is in the first covering position, the needle is exposable along the longitudinal direction when the needle cover is in the second uncovering position, and the needle is unexposed when the needle cover is in the third covering position,
    wherein an abutment on the at least one longitudinally extending arm of the housing is receivable within the at least one opening along the longitudinal direction of the needle cover when the needle cover is biased into the third covering position,
    wherein the at least one longitudinally extending arm of the housing extends inwardly from the housing when the at least one longitudinally extending arm is in the second position, the at least one longitudinally extending arm being in the second position when the needle cover is in the third covering position, and
    wherein a proximal end of the housing includes an opening, the needle cover extending through the opening of the housing.

2. The auto-injection device of claim 1, further comprising an opening located along a proximal end of the needle cover, wherein a proximal end of the needle is movable through the opening of the needle cover when the needle cover is moved to the second uncovering position.

3. The auto-injection device of claim 2, further comprising a needle sheath disposed between the proximal end of the needle cover and the proximal end of the cartridge, the needle being at least partially disposed within the needle sheath, wherein the needle sheath is pierced by the needle when the needle cover is moved from the first covering position to the second uncovering position.

4. The auto-injection device of claim 1, wherein the at least one longitudinally extending arm of the housing is flexible between the first position and the second position, such that in the first position, the at least one longitudinally extending arm extends inwardly from the housing at a first angle and in the second position, the at least one longitudinally extending arm extends inwardly from the housing at a second angle.

5. The auto-injection device of claim 4, wherein the first angle is from about 0 degrees to about 5 degrees, and wherein the second angle is from about 5 degrees to about 15 degrees.

6. The auto-injection device of claim 1, wherein the needle is fixed to the cartridge.

7. The auto-injection device of claim 1, further comprising at least one outwardly extending abutment on an exterior surface of the cartridge and at least one projection extending along an interior surface of the needle cover, wherein the at least one outwardly extending abutment is configured to abut the at least one projection extending along the interior surface of the needle cover.

8. The auto-injection device of claim 1, further comprising a removable safety, wherein the removable safety prevents movement of the needle cover from the first covering position to the second uncovering position, prevents movement of the cartridge from a first cartridge position to a second cartridge position, or both when in place on the auto-injection device.

9. The auto-injection device of claim 8, further comprising:
    a plunger, a proximal end of the plunger being attached to the stopper;
    an end stop; and
    a retainer,
    wherein the safety is configured to be removably inserted into a distal end of the plunger, such that when the safety is removed from the plunger, the retainer is movable towards the distal end of the auto-injection device such that the end stop is engageable around the distal end of the plunger and the plunger is then removable from the retainer.

10. The auto-injection device of claim 9, wherein the retainer is movable towards the distal end of the auto-injection device by a distal end of the needle cover, the distal end of the needle cover abutting against the retainer when the needle cover moves from the first covering position to the second uncovering position.

11. The auto-injection device of claim 9, further comprising:
    a first biasing element, wherein a proximal end of the first biasing element exerts a force on a circumferential flange of the plunger and a distal end of the first biasing element exerts a force on the retainer; and a second biasing element, wherein a proximal end of the second biasing element exerts a force on a circumferential flange on an exterior surface of the needle cover and a distal end of the second biasing element exerts a force on a flange on an interior surface of the housing.

12. A method for delivering a dose of fluid medicament via an auto-injection device, wherein the auto-injection device defines a longitudinal direction and comprises a housing comprising an opening at a proximal end of the housing and at least one longitudinally extending arm, the at least one longitudinally extending arm being flexible between a first position and a second position; a cartridge movable along the longitudinal direction relative to the housing, the cartridge containing a fluid medicament contained between a stopper and a proximal end of the cartridge, wherein the stopper includes a recess located at a distal end of the stopper; a needle located at a proximal end of the auto-injection device: a needle cover movable along the longitudinal direction relative to the housing between the proximal end of the auto-injection device and a distal end of the auto-injection device, the needle cover extending through the opening of the housing and comprising at least one opening along the longitudinal direction; and a plunger, a proximal end of the plunger being engaged in the recess at the distal end of the stopper; the method comprising:

pressing the proximal end of the auto-injection device against a surface of skin, wherein the longitudinal direction of the auto-injection device is generally perpendicular to the surface of skin, and wherein the at least one longitudinally extending arm is in the first position, such that the needle cover moves from a first covering position to a second uncovering position and the cartridge moves from a first cartridge position to a second cartridge position;

piercing the surface of skin and underlying tissue with a proximal end of the needle by continuing to press the proximal end of the auto-injection device against the surface of skin such that the cartridge moves from the second cartridge position to a third cartridge position;

delivering the fluid medicament by continuing to press the proximal end of the auto-injection device against the surface of skin until a circumferential flange of the plunger abuts a circumferential flange on an interior surface of the cartridge; and removing the proximal end of the auto-injection device from the surface of skin after the fluid medicament is delivered such that the needle cover is biased from the second uncovering position into a third covering position and the at least one longitudinally extending arm of the housing is received within the at least one opening along the longitudinal direction of the needle cover, such that the needle is unexposed and the at least one longitudinally extending arm of the housing is moved to the second position, the at least one longitudinally extending arm of the housing extending inwardly from the housing when the at least one longitudinally extending arm is in the second position.

13. The method of claim 12, wherein the at least one longitudinally extending arm extends inwardly from the housing at an angle of from about 0 degrees to about 5 degrees in the first position, and wherein the at least one longitudinally extending arm extends inwardly from the housing at an angle of from about 5 degrees to about 15 degrees in the second position.

14. The method of claim 12, wherein
the proximal end of the cartridge includes an opening, wherein a distal end of the needle is contained within the opening of the cartridge.

15. The method of claim 12, wherein the auto-injection device further comprises a needle sheath disposed between a proximal end of the needle cover and the proximal end of the cartridge, the needle being at least partially disposed within the needle sheath such that when the needle cover moves from the first covering position to the second uncovering position, the needle sheath is pierced by the needle.

16. The method of claim 12, wherein the auto-injection device further comprises an end stop; a retainer; and a safety, the safety being insertable into a distal end of the plunger such that the safety prevents the needle cover from sliding against the housing, prevents the cartridge from sliding against the needle cover, or both when in place on the auto-injection device;

the method further comprising removing the safety prior to positioning the proximal end of the auto-injection device against the surface of skin such that when the needle cover moves from the first covering position to the second uncovering position, a distal end of the needle cover moves the retainer towards the distal end of the auto-injection device, the end stop engages around the distal end of the plunger, and the plunger is removable from the retainer.

17. The method of claim 16, wherein a proximal end of a first biasing element exerts a force on the circumferential flange of the plunger and a distal end of the first biasing element exerts a force on the retainer to move the cartridge towards the third cartridge position and to facilitate delivery of the fluid medicament when the cartridge is in the third cartridge position, and wherein a proximal end of a second biasing element exerts a force on a circumferential flange on an exterior surface of the needle cover and a distal end of the second biasing element exerts a force on a circumferential flange on an interior surface of the housing to bias the needle cover towards the third covering position.

18. The method of claim 12, wherein the fluid medicament contains epinephrine or naloxone.

\* \* \* \* \*